United States Patent
Taferner

(10) Patent No.: US 9,804,102 B2
(45) Date of Patent: Oct. 31, 2017

(54) DEVICE FOR TESTING DUCTS

(71) Applicant: Marko Taferner, Wolfnitz (AT)

(72) Inventor: Marko Taferner, Wolfnitz (AT)

( * ) Notice: Subject to any disclaimer, the term of this patent is extended or adjusted under 35 U.S.C. 154(b) by 0 days.

(21) Appl. No.: 14/787,112

(22) PCT Filed: Sep. 25, 2014

(86) PCT No.: PCT/AT2014/000173
§ 371 (c)(1),
(2) Date: Oct. 26, 2015

(87) PCT Pub. No.: WO2015/077805
PCT Pub. Date: Jun. 4, 2015

(65) Prior Publication Data
US 2016/0069821 A1    Mar. 10, 2016

(30) Foreign Application Priority Data
Nov. 28, 2013 (AT) .................................. A 911/2013

(51) Int. Cl.
*G01N 21/00* (2006.01)
*G01N 21/954* (2006.01)
(Continued)

(52) U.S. Cl.
CPC ............ *G01N 21/954* (2013.01); *F16L 55/48* (2013.01); *G01M 3/005* (2013.01); *G01M 3/246* (2013.01); *G01N 2021/9544* (2013.01)

(58) Field of Classification Search
CPC ................. G01N 27/82; G01N 29/225; G01N 2291/2634; G01N 29/265;
(Continued)

(56) References Cited

U.S. PATENT DOCUMENTS 6,880,195 B1   4/2005   Bahari et al.
8,307,725 B2   11/2012  Stubler et al.
(Continued)

FOREIGN PATENT DOCUMENTS

DE   691 02 924 T2   11/1994
DE   696 18 784 T2    9/2002
(Continued)

OTHER PUBLICATIONS

International Search Report, dated Jan. 26, 2015, from corresponding PCT Application.
(Continued)

*Primary Examiner* — Michael P Stafira
(74) *Attorney, Agent, or Firm* — Young & Thompson

(57) ABSTRACT

A device (1) for registering data and features of ducts includes at least one camera (3, 5), at least one distance measurement apparatus and at least one apparatus for measuring properties of the medium contained in the duct. Furthermore, provision can be made for an illumination apparatus (4), a tracking sensor (10), which emits data in relation to the current position of the device (1), and an inclination measurement device (inclinometer and gyroscopic compass 9). The device can have a passive or active drive for moving the device (1) along the duct. The device (1) can register a length recording of the duct with the aid of photo geometry or with sound, radar, acceleration sensors and/or mechanical distance measurements. Thus, after a duct has been inspected, each point can be assigned precisely in terms of length.

20 Claims, 3 Drawing Sheets

(51) Int. Cl.
*G01M 3/00* (2006.01)
*G01M 3/24* (2006.01)
*F16L 55/48* (2006.01)

(58) Field of Classification Search
CPC ........... G01N 2291/2636; G01N 27/83; G01N 29/04; G01N 29/2412; G01N 2291/023; G01N 2291/0258; G01N 2291/02854; G01N 2291/0289; G01N 29/043
See application file for complete search history.

(56) References Cited

U.S. PATENT DOCUMENTS

| | | | | |
|---|---|---|---|---|
| 2002/0033019 A1* | 3/2002 | Mizzi | ...................... | F03B 17/00 60/398 |
| 2004/0173116 A1* | 9/2004 | Ghorbel | .................. | F16L 55/26 104/138.2 |
| 2005/0288819 A1 | 12/2005 | De Guzman | | |
| 2007/0022935 A1* | 2/2007 | Griffith | ................... | B63C 11/02 114/312 |
| 2007/0203623 A1* | 8/2007 | Saunders | ............. | G05D 1/0206 701/23 |
| 2008/0264323 A1* | 10/2008 | Gosling | ................... | B63G 8/08 114/330 |
| 2010/0041285 A1* | 2/2010 | Riggs | ..................... | B63H 21/17 440/6 |
| 2011/0185519 A1* | 8/2011 | Heard | .................. | A01K 61/007 15/1.7 |
| 2012/0048172 A1* | 3/2012 | Lotz | ......................... | B63G 8/16 114/330 |
| 2012/0183114 A1* | 7/2012 | Bischoff | ................. | F16L 55/32 376/248 |
| 2012/0215348 A1 | 8/2012 | Skrinde | | |
| 2012/0236978 A1* | 9/2012 | Foley | .................... | G21C 17/003 376/260 |
| 2013/0082866 A1 | 4/2013 | Jaganathan et al. | | |
| 2014/0061376 A1* | 3/2014 | Fisher | ...................... | B60K 1/00 244/62 |
| 2014/0098215 A1* | 4/2014 | Dinis | ...................... | B63C 11/02 348/81 |
| 2014/0107862 A1* | 4/2014 | Jung | ........................ | B63G 7/00 701/1 |

FOREIGN PATENT DOCUMENTS

| | | |
|---|---|---|
| DE | 600 09 049 T2 | 10/2004 |
| DE | 10 2008 010 438 A1 | 8/2009 |
| GB | 2492460 | 1/2013 |
| GB | 2492460 A | 1/2013 |
| KR | 1020090046415 A | 5/2009 |
| WO | 02/070943 A2 | 9/2002 |
| WO | 02070943 | 9/2002 |
| WO | 2013/088427 A1 | 6/2013 |

OTHER PUBLICATIONS

Austrian Search Report, dated Oct. 27, 2014, from corresponding Austrian Application.
European Office Action dated Sep. 27, 2016; Application No. 14 792 369.2.
European Search Report dated Dec. 19, 2016; Application No. 16185169.6.

* cited by examiner

DEVICE FOR TESTING DUCTS

The invention relates to a device for registering data and features of ducts.

SUMMARY OF THE INVENTION

There is a need for devices that can be used to register data of ducts and their features (properties).

The object of the invention is to provide such a device. This object is accomplished according to the invention described below and recited by the appended claims.

Preferred and advantageous configurations of the invention are further described in the description that follows and the appended claims.

The use of the device according to the invention makes it possible to register data from any desired ducts and, in potential embodiments of the device according to the invention, also data from media contained in the duct or transported through the duct, and to transmit said data for analysis.

In the present context, ducts include, e.g., gravity wastewater channels, wastewater (pumping) pressure lines, water lines, and pressure lines for liquid and gaseous media, including but not limited to drinking water pipelines, oil lines (pipelines), district heating pipelines, gas pipelines, cable conduits, power plant pipelines, or any other industrial pipes.

The device according to the invention is especially a universally usable, preferably buoyant, optical measuring device, which can be configured according to the type of duct and the type of medium conveyed within the duct.

In particular, the device according to the invention pertains to an examination device, preferably buoyant, for pipelines, whereby, for example, a camera is provided that takes pictures and videos of the duct being examined, saves them, or immediately relays them for evaluation.

The device according to the invention can also be configured such that it can compile a length recording of the duct with the aid of photo-geometry or with sound, radar, acceleration sensors, mechanical distance measurements, or a combination of these. Any point can thus, after an inspection of a pipeline has been made, be precisely placed in terms of length.

The device according to the invention can be deployed without interrupting the use of the duct that is to be examined.

The use of the device according to the invention does not require the duct to be cleaned.

The device according to the invention makes possible an affordable examination of ducts, especially a pre-examination of channels, even in places that are difficult to access.

The device according to the invention is configured such that it can work while floating. In one embodiment, the device according to the invention floats freely without cables in the flow of media inside the duct.

Using the device according to the invention, it is possible—depending upon the Embodiment—to:
  assess the state of deposits,
  perform a visual inspection of deformations of the duct,
  determine high points of the duct,
  make an optical assessment of the interior of the duct,
  locate leaks without external noise interference,
  directly record leak noises,
  locate leaks even in pipes that are difficult to access.

In embodiments, the device according to the invention can have the following sensors:
  Pressure transmitter for pressure recording inside a pipe that is in use, so that hydraulic models of the pipeline can be captured,
  noise-level sensors to measure noise levels,
  turbidity sensors,
  conductivity sensors,
  inclinometer and gyrocompass for reconstructing and locating the duct flow,
  devices for measuring wall thickness,
  locating equipment for the device,
  temperature sensor.

The device according to the invention can be outfitted with a drive in order to move the device further inside of the duct that is to be examined. In gravity ducts or fall pipes, the forward movement can, for example, take place primarily by having the device according to the invention float with the medium that is flowing inside the duct.

In pressure ducts, the device can be outfitted with equipment in the manner of screens (umbrellas) in order to move the device along through the flowing medium.

One further possibility for moving the device along inside of the duct is to provide a drive propeller that is coupled to an electric motor.

When the device according to the invention is deployed inside of a gravity wastewater channel, it is introduced as a floating device inside a sewage line and then floats in the direction of the flow with the feces-containing water present in the channel. In this way, depending on the flow rate, the device can cover 0.01 to over 30 kilometers per hour, and it is then removed from the channel at the shaft at the end of the duct section that is to be examined.

The data collected by the device subsequently either can be read via Bluetooth, radio, or another form of data transmission or the data can be transferred from the data storage medium contained in the device to a computer (PC). Further evaluation can be done using appropriate software via an interface for GIS (duct registry).

The following data can, for example, be collected inside gravity wastewater channels:
  Temperature measurement for inflow measurement,
  visual inspection,
  length measurement,
  inclinometer,
  location sensor: an electronic standard sensor (for example: 32.8 kHz), which can be located with pinpoint accuracy using a duct-location device, so that the position of the device can be determined in real time.

When deployed in drinking water and pressure ducts (up to 100 bar), the device according to the invention can perform the following examinations:
  Visual inspection,
  length measurement,
  acoustic examination for potential leaks (drip loss, leakage) with information as to the location of the leak, measured from the point of origin or the nearest valve (gate valve, valve flap, tapping clamp, vent plug, etc.),
  conductivity sensor,
  turbidity sensor,
  device for measuring wall thickness,
  inclinometer measurements and gyrocompass for reconstructing and locating the duct flow,
  pressure sensor,
  temperature sensor.

Forward movement of the device according to the invention inside of a drinking water duct or pressure duct up to 100 bar can occur as has been described above for gravity wastewater channels. This is likewise true for the evaluation of the data.

When a device according to the invention is deployed inside industrial pipes (up to 100 bar of pressure), the device according to the invention may be introduced into the pressure line while this line is in use, and under operating pressure, the device can perform the following examinations:

Visual inspection,
length measurement,
acoustic examination of potential leaks and drip loss up to leakage with indication of the position of the leak or leakage,
conductivity sensor,
pressure sensor,
temperature,
acoustic examination of leaks,
turbidity sensor,
device for measuring wall thickness,
inclinometer measurements and gyrocompass.

Depending on the flow rate of the medium inside an industrial pipe, the device according to the invention can cover between 0.01 and 30 kilometers per hour, and the device is extracted at the end of the stretch of the industrial pipe that is to be investigated. The data collected by the device concerning the industrial pipe or the medium conveyed in the pipeline is/are either read via Bluetooth, radio, or another form of data transmission or the data are transferred via the data storage medium contained in the device to a computer (PC). Evaluation of the collected data can be done using analysis software with an interface for GIS (duct registry).

When a device according to the invention is employed for registering data and features of a gas pipeline, the measuring device can perform, for example, the following examinations:

Visual inspection,
length measurement,
acoustic examination of potential leaks and drip loss up to leakage with indication of the position of the leak or leakage,
conductivity sensor,
turbidity sensor,
device for measuring wall thickness,
inclinometer measurements and gyrocompass.

Depending on the flow rate of the medium inside a gas pipe, the device according to the invention can cover between 0.01 and 30 kilometers per hour, and the device is extracted at the end of the stretch of the gas pipe that is to be investigated. The data collected by the device concerning the gas pipe or the medium conveyed in the pipe is/are either read via Bluetooth, radio, or another form of data transmission or the data are transferred via the data storage medium contained in the device to a computer (PC). Evaluation of the collected data can be done using analysis software with an interface for GIS (duct registry).

When a device according to the invention is configured to be employed in pipelines for district heating, it is possible to deploy the device with the duct in operation, whereby the following examinations can be performed:

Visual inspection,
length measurement,
acoustic examination of potential leaks and drip loss up to leakage with indication of the position of the leak or leakage,
conductivity sensor,
turbidity sensor,
device for measuring wall thickness,
inclinometer measurements and gyrocompass.

Depending on the flow rate of the medium inside a pipeline for district heating, the device according to the invention can cover between 0.01 and 30 kilometers per hour, and the device is extracted at the end of the stretch of pipeline for district heating that is to be investigated. The data collected by the device concerning the pipeline for district heating or the medium conveyed in the pipeline is/are either read via Bluetooth, radio, or another form of data transmission or the data are transferred via the data storage medium contained in the device to a computer (PC). The evaluation of the collected data can be done using analysis software with an interface for GIS (duct registry).

In a further embodiment, the device according to the invention can be called upon to examine oil lines (pipelines), whereby the device may likewise work here while the pipelines are in operation in order to perform, for example, the following examinations:

Visual inspection,
length measurement,
acoustic examination of potential leaks and drip loss up to leakage with indication of the position of the leak or leakage,
conductivity sensor,
turbidity sensor,
device for measuring wall thickness,
inclinometer measurements and gyrocompass,
pressure sensor.

Depending on the flow speed of the medium inside an oil line (pipeline), the device according to the invention can cover between 0.01 and 30 kilometers per hour, and the device is extracted from the oil line (pipeline) at the end of the stretch that is to be investigated. The data collected by the device concerning the oil line (pipeline), or the medium conveyed in the pipeline is/are either read via Bluetooth, radio, or another form of data transmission or the data are transferred via the data storage medium contained in the device to a computer (PC). Evaluation of the collected data can be done using analysis software with an interface for GIS (duct registry).

BRIEF DESCRIPTION OF THE DRAWINGS

Further details and features of the invention are hereinafter explained with reference to the embodiments shown in the drawings. Here.

DETAILED DESCRIPTION OF THE PREFERRED EMBODIMENTS

Figure 1:
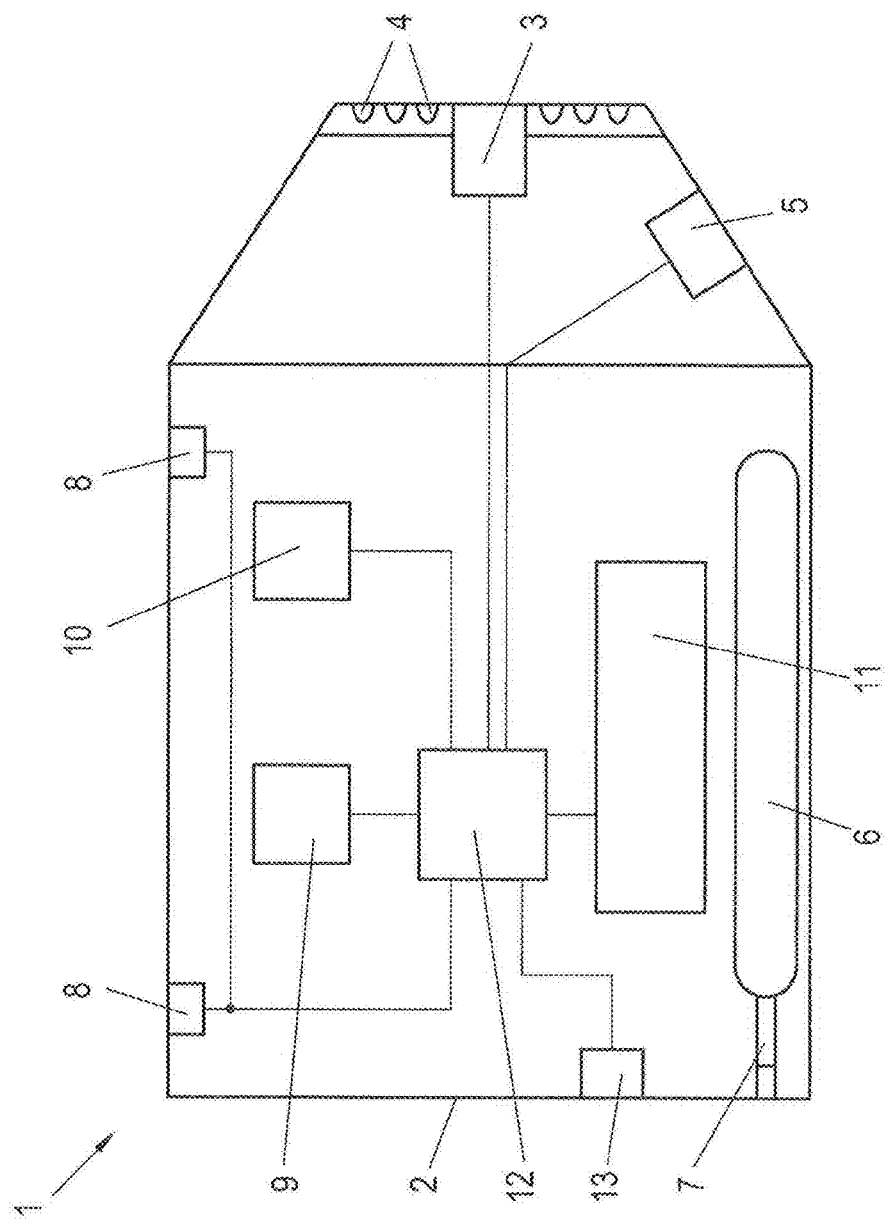
FIG. 1 schematically shows a device according to the invention.

A device 1 according to the invention has, in the embodiment shown in FIG. 1, a casing 2. On the one end—the front end, based on the direction of movement during an examination of a duct—a camera 3 is provided. The camera 3 is provided with an illumination apparatus 4, for example, encircling the camera 3, which illumination apparatus 4 is, for example, configured as an LED-illumination unit.

Additionally, the device 1 can have another camera 5 that has a different viewing angle than that of the camera 3 arranged on the front end. Since the device 1 according to the invention is supposed to float, for example, in a liquid medium, it has an air bladder 6 that communicates with the region outside of the casing 2, i.e., outside of the device 1, via a duct 7 that ends in the wall of the casing 2.

The embodiment of the device 1 shown in FIG. 1 further comprises two sensors 8 for a distance measurement apparatus that make it possible to measure the distance covered by the device 1.

An inclinometer and/or gyrocompass 9 and a tracking sensor 10 are arranged in the interior of the casing. The power supply for the different components of the device according to the invention is provided by an energy storage device 11 provided in the casing 2, for example a storage battery. All apparatuses of the device according to the invention, such as the cameras 3 and 5, the sensors 8 of the distance measurement apparatus, the radar sensor, the speed sensor and temperature sensor 13, the inclinometer and gyrocompass 9, and the tracking sensor 10, are operatively connected to a data logger and a control unit 12.

Figure 2:
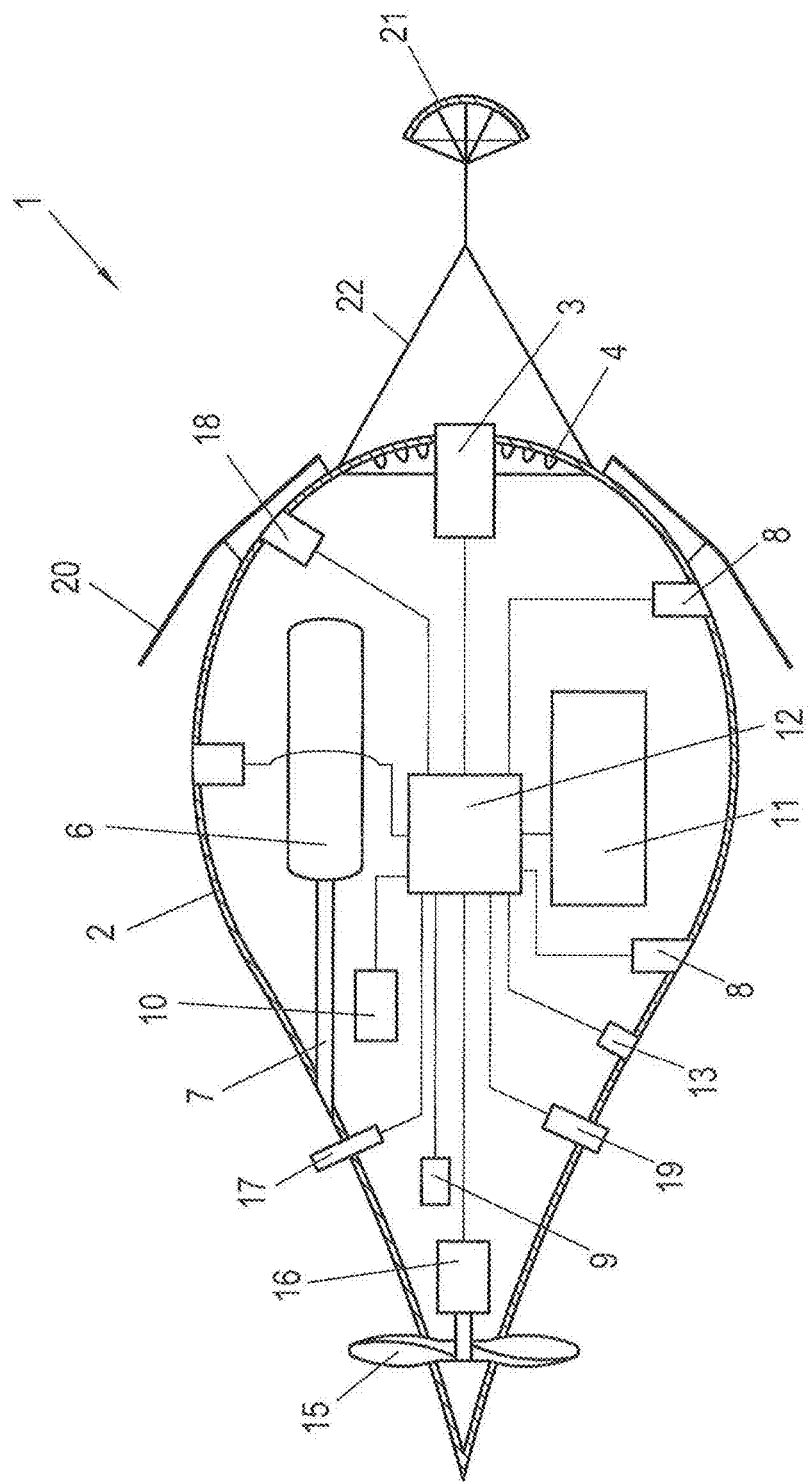
FIG. 2 schematically shows a modified embodiment of a device according to the invention.

The embodiment of a device 1 according to the invention shown in FIG. 2 comprises a casing 2, which in this embodiment is designed to be streamlined. Again, the device 1 of the embodiment of FIG. 2 has a camera 3 and an illumination unit 4 assigned to this camera 3, the air bladder 6, the sensors 8 of the distance measurement apparatus, the radar sensor, the speed sensor and temperature sensor 13, the inclinometer and gyrocompass 9, and the location transmitter 10.

The embodiment shown in FIG. 2 of the device 1 according to the invention further comprises, as an active drive, a propeller 15 with a drive motor 16 that is provided with power from the energy storage device 11.

In place of or in addition to the active drive of the device 1 in the form of the propeller 15, a circular screen 20 can be provided as a passive drive, especially in the region of the front end, where the camera 3 is arranged, in order to propel the device 1 using the medium flowing through the duct.

The screen 20 can be replaced or complemented by a parasail 21 that is connected to the front end of the device 1 by the connecting elements 22.

Further, the embodiment shown in FIG. 2 of a device 1 according to the invention has a conductivity sensor 17 and an acoustic pickup sensor 18. Finally, in the device 1 according to the invention of the embodiment of FIG. 2, a turbidity sensor 19 is provided.

The device according to the invention can also be provided with an apparatus for measuring the flow rate of the medium through the duct that is to be examined.

The device according to the invention can also be equipped with an acceleration sensor, so that in combination with other sensors (for example, the radar sensor), the current speed at which the device 1 is moving can be determined.

Additionally, the speed of the device 1 can be determined by measuring the image geometry of the pipe segments (measuring the length and time).

Figure 3:
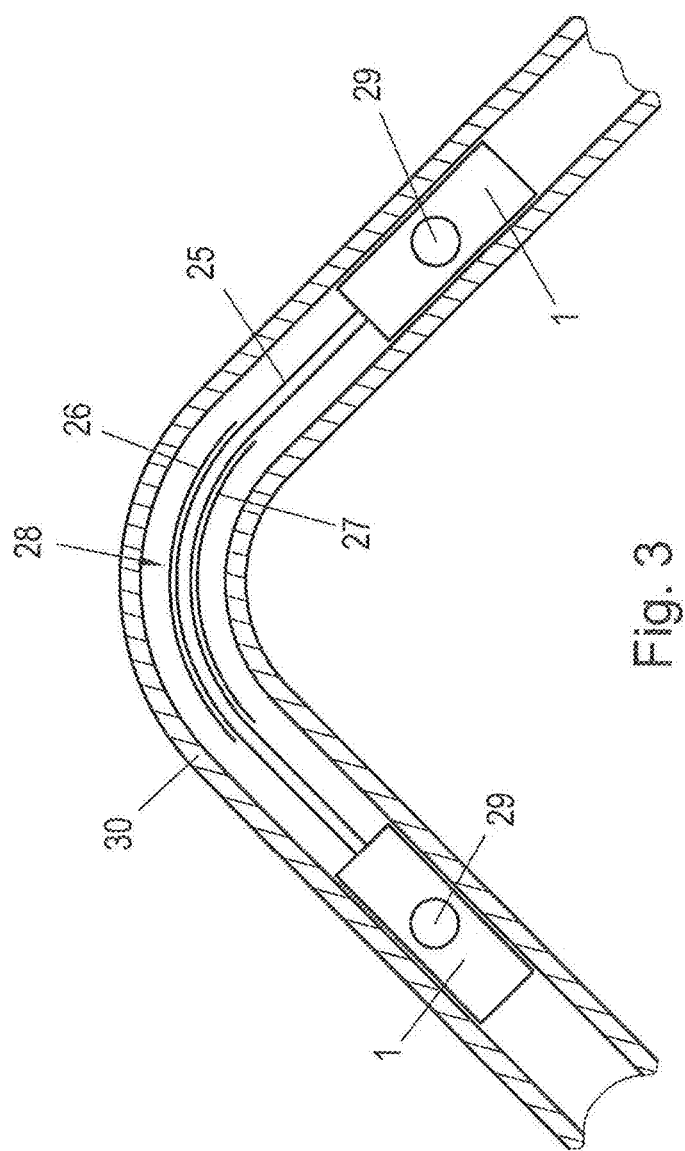
FIG. 3 shows an application example of devices according to the invention.

FIG. 3 shows an application example comprising two devices 1 according to the invention that are connected to each other by a flexible (not length-adjustable) element 25. At least two diametrically opposite sensors 26, 27 that extend in the lengthwise direction of the element 25 and that register length changes, e.g., strain gauges, are provided on the element 25. When the element 25 is bent (e.g., bend 28 in FIG. 3), the sensor 26 that lies on the outer curve is extended (stretched) and the sensor 27 that lies on the inner curve is shortened (compressed). These length changes of the sensors 26, 27 are registered and, in connection with gyrocompass-apparatuses 29 in the devices 1, make it possible to register the course of the duct 30.

In summary, one embodiment of the invention can be described as follows:

A device 1 for registering data and features of ducts comprises at least one camera 3, 5, at least one distance measurement apparatus, and at least one apparatus for measuring properties of the medium contained in the duct. Furthermore, provision can be made for an illumination apparatus 4, a location sensor 10, which emits data relating to the current position of the device 1, and an inclination measurement device (inclinometer and gyroscopic compass 9). The device can have a passive or an active drive for moving the device 1 along the duct. The device 1 can register a length recording of the duct with the aid of photo-geometry or with sound, radar, acceleration sensors and/or mechanical distance measurements. Thus, after a duct has been inspected, any point can be assigned precisely in terms of length.

The invention claimed is:

1. A device (1) for examining an interior of ducts and registering data and features of the ducts, comprising:
    sensing instruments, including
        at least one camera (3, 5),
        at least one distance measurement apparatus,
        at least one apparatus for measuring properties of the medium contained in the duct, said at least one apparatus being at least one selected from the group consisting of a conductivity sensor (17) and a turbidity sensor (19),
        a location transmitter (10) that emits data relating to the current position of the device (1), the location transmitter (10) being an electronic transmitter configured to communicate with a duct locator, and
        an acoustic pick-up sensor (18) that registers leaks in the duct by drip loss or leakages;
    a control unit for controlling device in communication with the sensing instruments, the control unit having a storage medium for storing data received from the sensing instruments and configured to transfer data to an external data device;
    an illumination apparatus (4) assigned to the at least one camera (3, 5); and
    an energy storage device (11) configured to provide electrical power for supplying the device with energy,
    wherein the device (1) is configured to float freely in the flow of media in a duct being examined, an adjustable air bladder (6) being located in the device (1) configured to adjust a property of flotation of the device (1).
2. The device according to claim 1, further comprising:
    an inclination measurement device, comprised of an inclinometer and a gyroscopic compass (9), configured to capture a path of the duct.
3. The device according to claim 1, wherein the air bladder (6) is configured to communicate with a liquid that is contained in the duct.
4. The device according to claim 1, further comprising:
    a casing (2), in or on which the elements and components of the device (1) are provided.
5. The device according to claim 1, wherein a transmitter is provided in communication with the control unit configured to relay data stored by the control unit concerning the duct wirelessly to an evaluation device external to the device.

6. The device according to claim 1, further comprising:
   equipment for measuring a wall thickness of the duct being examined.

7. The device according to claim 2, wherein the air bladder (6) is configured to communicate with a liquid that is contained in the duct.

8. The device according to claim 2, further comprising:
   a casing (2), in or on which the elements and components of the device (1) are provided.

9. The device according to claim 3, further comprising:
   a casing (2), in or on which the elements and components of the device (1) are provided.

10. The device according to claim 2, wherein a transmitter is provided in communication with the control unit configured to relay data stored by the control unit concerning the duct wirelessly to an evaluation device external to the device.

11. The device according to claim 3, wherein a transmitter is provided in communication with the control unit configured to relay data stored by the control unit concerning the duct wirelessly to an evaluation device external to the device.

12. The device according to claim 4, wherein a transmitter is provided in communication with the control unit configured to relay data stored by the control unit concerning the duct wirelessly to an evaluation device external to the device.

13. The device according to claim 2, further comprising:
    equipment for measuring a wall thickness of the duct being examined.

14. The device according to claim 3, further comprising:
    equipment for measuring a wall thickness of the duct being examined.

15. The device according to claim 4, further comprising:
    equipment for measuring a wall thickness of the duct being examined.

16. The device according to claim 5, further comprising:
    equipment for measuring a wall thickness of the duct being examined.

17. The device according to claim 4, wherein the air bladder is in communication with a region outside the casing by way of a duct that terminates at an exterior wall of the casing.

18. The device according to claim 17, further comprising:
    an inclination measurement device, comprised of an inclinometer and a gyroscopic compass (9), configured to capture a path of the duct.

19. The device according to claim 18, further comprising:
    equipment for measuring a wall thickness of the duct being examined.

20. The device according to claim 19, wherein the air bladder (6) is configured to communicate with a liquid that is contained in the duct.

* * * * *